(12) United States Patent
Allen et al.

(10) Patent No.: US 9,707,049 B1
(45) Date of Patent: Jul. 18, 2017

(54) STEREOTACTIC DEVICE FOR IMPLANTATION OF PERMANENT IMPLANTS INTO A RODENT BRAIN

(71) Applicants: Timothy Allen, Coral Gables, FL (US); Bruce McNaughton, Irvine, CA (US); Meifung Su, Miami, FL (US); Leila Mangan Allen, Coral Gables, FL (US)

(72) Inventors: Timothy Allen, Coral Gables, FL (US); Bruce McNaughton, Irvine, CA (US); Meifung Su, Miami, FL (US); Leila Mangan Allen, Coral Gables, FL (US)

(73) Assignees: The Florida International University Board of Trustees, Miami, FL (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 15/387,843

(22) Filed: Dec. 22, 2016

(51) Int. Cl.
*A61B 19/00* (2006.01)
*A61B 90/11* (2016.01)
*A61B 90/14* (2016.01)
*A61B 90/00* (2016.01)
*A61B 17/16* (2006.01)
*A61B 90/10* (2016.01)

(52) U.S. Cl.
CPC .......... *A61B 90/11* (2016.02); *A61B 17/1695* (2013.01); *A61B 90/14* (2016.02); *A61B 90/361* (2016.02); *A61B 2090/103* (2016.02); *A61B 2090/363* (2016.02); *A61B 2503/40* (2013.01)

(58) Field of Classification Search
CPC ....... A61B 90/11; A61B 90/14; A61B 90/361; A61B 17/1695; A61B 2090/363; A61B 2090/103; A61B 2503/40
USPC ........................................................... 90/14
See application file for complete search history.

(56) References Cited

U.S. PATENT DOCUMENTS

| | | | | |
|---|---|---|---|---|
| 3,016,899 A | * | 1/1962 | Stenvall | A61B 90/11 378/162 |
| 3,021,842 A | * | 2/1962 | Flood | A61B 90/11 604/175 |
| 3,061,936 A | * | 11/1962 | Dobbeleer | A61B 6/501 269/71 |
| 3,223,087 A | * | 12/1965 | Vladyka | A61B 90/11 33/512 |
| 3,357,431 A | * | 12/1967 | Newell | A61B 90/11 606/130 |
| 3,374,548 A | * | 3/1968 | Romney | A61B 90/11 33/23.01 |

(Continued)

*Primary Examiner* — Amy R Weisberg
(74) *Attorney, Agent, or Firm* — Saliwanchik, Lloyd & Eisenschenk

(57) ABSTRACT

Stereotactic systems and implantation methods that can be designed for use with a specific species and further customized for use with an individual within the species are provided. The stereotactic system can include an implant jig that can model a tissue or organ in which a target tissue area is located. A neurocap can be coupled to the implant jig for pre-planning and pre-placement of implants. A stencil can be used to determine the location for placement of the neurocap on the individual, so that the implants can be precisely targeted at the desired location. Pre-surgical information and data can be obtained from an individual and used to customize components of a stereotactic system, which can improve accuracy of implant placement.

5 Claims, 15 Drawing Sheets

(56) References Cited

U.S. PATENT DOCUMENTS

| | | | | |
|---|---|---|---|---|
| 3,384,086 A * | 5/1968 | Rocha-Miranda | A61B 90/11 | 606/130 |
| 3,457,922 A * | 7/1969 | Ray | A61B 90/11 | 378/162 |
| 3,508,552 A * | 4/1970 | Hainault | A61B 6/022 | 33/512 |
| 3,817,249 A * | 6/1974 | Nicholson | A61B 90/11 | 606/129 |
| 4,228,799 A * | 10/1980 | Anichkov | A61B 90/10 | 378/162 |
| 4,341,220 A * | 7/1982 | Perry | A61B 90/11 | 378/162 |
| 4,350,159 A * | 9/1982 | Gouda | A61B 90/11 | 606/129 |
| 4,386,602 A * | 6/1983 | Sheldon | A61B 17/0293 | 600/102 |
| 4,463,758 A * | 8/1984 | Patil | A61B 6/501 | 33/515 |
| 4,592,352 A * | 6/1986 | Patil | A61B 90/11 | 5/637 |
| 4,608,977 A * | 9/1986 | Brown | A61B 90/11 | 378/162 |
| 4,618,978 A * | 10/1986 | Cosman | A61B 6/08 | 324/309 |
| 4,706,665 A * | 11/1987 | Gouda | A61B 90/11 | 604/116 |
| 4,834,089 A * | 5/1989 | Koivukangas | A61B 8/0808 | 604/175 |
| 5,004,457 A * | 4/1991 | Wyatt | A61B 90/11 | 604/117 |
| 5,006,122 A * | 4/1991 | Wyatt | A61B 90/11 | 128/DIG. 26 |
| 5,030,223 A * | 7/1991 | Anderson | A61B 90/11 | 600/383 |
| 5,047,036 A * | 9/1991 | Koutrouvelis | A61B 90/11 | 606/1 |
| 5,080,662 A * | 1/1992 | Paul | A61B 90/11 | 606/130 |
| 5,116,345 A * | 5/1992 | Jewell | A61B 90/11 | 606/130 |
| 5,143,076 A * | 9/1992 | Hardy | A61N 5/1031 | 600/407 |
| 5,147,372 A * | 9/1992 | Nymark | A61B 17/3403 | 378/197 |
| 5,154,723 A * | 10/1992 | Kubota | A61G 13/12 | 600/102 |
| 5,163,430 A * | 11/1992 | Carol | A61B 90/11 | 378/20 |
| 5,176,689 A * | 1/1993 | Hardy | A61N 5/1031 | 378/206 |
| 5,201,742 A * | 4/1993 | Hasson | A61B 90/11 | 606/1 |
| 5,257,998 A * | 11/1993 | Ota | A61B 90/11 | 414/917 |
| 5,308,352 A * | 5/1994 | Koutrouvelis | A61B 17/3403 | 604/116 |
| 5,441,505 A * | 8/1995 | Nakamura | F16M 11/08 | 414/917 |
| 5,665,095 A * | 9/1997 | Jacobson | A61B 90/11 | 604/116 |
| 5,682,892 A * | 11/1997 | Selder | A61B 90/11 | 324/318 |
| 5,690,108 A * | 11/1997 | Chakeres | A61B 6/0442 | 378/20 |
| 5,752,962 A * | 5/1998 | D'Urso | A61B 90/11 | 128/857 |
| 5,776,143 A * | 7/1998 | Adams | A61B 90/11 | 606/130 |
| 5,957,934 A * | 9/1999 | Rapoport | A61B 90/11 | 600/417 |
| 5,984,930 A * | 11/1999 | Maciunas | A61B 90/11 | 600/417 |
| 6,011,996 A * | 1/2000 | Gielen | A61N 1/0529 | 600/378 |
| 6,110,182 A * | 8/2000 | Mowlai-Ashtiani | A61B 90/11 | 600/417 |
| 6,132,437 A * | 10/2000 | Omurtag | A61B 90/11 | 600/417 |
| 6,221,082 B1 * | 4/2001 | Marino | A61B 17/1757 | 606/130 |
| 6,261,299 B1 * | 7/2001 | Chakeres | A61B 90/10 | 606/130 |
| 6,327,491 B1 * | 12/2001 | Franklin | A61B 34/20 | 600/429 |
| 6,491,699 B1 * | 12/2002 | Henderson | A61B 19/52 | 600/414 |
| 6,529,765 B1 * | 3/2003 | Franck | A61B 90/10 | 600/427 |
| 6,589,254 B2 * | 7/2003 | Fontenot | A61B 90/17 | 600/231 |
| 6,689,142 B1 * | 2/2004 | Tremaglio, Jr. | A61B 17/3403 | 604/114 |
| 6,989,015 B2 * | 1/2006 | Daum | A61B 34/20 | 606/130 |
| 7,329,262 B2 * | 2/2008 | Gill | A61B 90/11 | 248/82 |
| 7,366,561 B2 * | 4/2008 | Mills | A61B 90/11 | 600/114 |
| 7,497,863 B2 * | 3/2009 | Solar | A61B 90/11 | 606/130 |
| 7,559,935 B2 * | 7/2009 | Solar | A61B 90/11 | 606/130 |
| 7,603,161 B2 * | 10/2009 | Wurmfeld | G01D 5/34723 | 600/424 |
| 7,636,596 B2 * | 12/2009 | Solar | A61B 90/11 | 600/429 |
| 7,744,606 B2 * | 6/2010 | Miller | A61B 90/11 | 606/130 |
| 7,776,048 B2 * | 8/2010 | Neubauer | A61B 90/11 | 606/86 R |
| 7,787,936 B2 * | 8/2010 | Kressy | A61B 90/10 | 600/407 |
| 7,879,045 B2 * | 2/2011 | Gielen | A61B 17/3403 | 606/129 |
| 7,892,243 B2 * | 2/2011 | Stuart | A61B 34/37 | 606/130 |
| 8,092,495 B2 * | 1/2012 | Boulis | A61B 17/0206 | 604/116 |
| 8,099,150 B2 * | 1/2012 | Piferi | A61B 5/055 | 324/318 |
| 8,298,245 B2 * | 10/2012 | Li | A61B 90/11 | 600/424 |
| 8,374,677 B2 * | 2/2013 | Piferi | G01R 33/286 | 600/417 |
| 8,414,597 B2 * | 4/2013 | Kao | A61B 19/26 | 606/130 |
| 8,435,250 B2 * | 5/2013 | Yoon | A61N 1/0529 | 310/323.06 |
| 8,548,569 B2 * | 10/2013 | Piferi | G01R 33/34046 | 600/407 |
| 8,617,180 B2 * | 12/2013 | Thiran | A61B 17/1739 | 600/424 |
| 8,657,761 B2 * | 2/2014 | Kim | A61B 10/0233 | 600/562 |
| 8,744,552 B2 * | 6/2014 | Akuzawa | A61B 10/0233 | 600/424 |
| 8,747,331 B2 * | 6/2014 | Luginbuhl | A61B 17/3403 | 600/562 |
| 8,747,419 B2 * | 6/2014 | Solar | A61B 17/00234 | 606/130 |
| 8,771,290 B2 * | 7/2014 | Mitchell | A61B 90/11 | 248/181.1 |
| 8,818,490 B2 * | 8/2014 | Martens | A61B 5/055 | 600/411 |
| 9,061,133 B2 * | 6/2015 | Wurster | A61N 7/02 | |
| 9,131,948 B2 * | 9/2015 | Fang | A61B 17/1671 | |
| 9,192,446 B2 * | 11/2015 | Piferi | A61B 19/201 | |
| 9,289,270 B2 * | 3/2016 | Gielen | A61B 34/20 | |

(56) References Cited

U.S. PATENT DOCUMENTS

| | | | |
|---|---|---|---|
| 9,345,875 B2* | 5/2016 | Appenrodt | A61N 1/0529 |
| 9,387,008 B2* | 7/2016 | Sarvestani | A61B 17/3403 |
| 9,468,751 B2* | 10/2016 | Bonde | A61N 1/0539 |
| 9,498,290 B2* | 11/2016 | Wham | A61N 1/0534 |
| 2003/0187351 A1* | 10/2003 | Franck | A61B 90/10 600/429 |
| 2006/0079886 A1* | 4/2006 | Orszulak | A61B 18/1206 606/41 |
| 2006/0079887 A1* | 4/2006 | Buysse | A61B 18/1206 606/41 |
| 2007/0078306 A1* | 4/2007 | Allison | A61N 5/103 600/300 |
| 2007/0203538 A1* | 8/2007 | Stone | A61N 1/37247 607/59 |
| 2007/0203539 A1* | 8/2007 | Stone | A61N 1/0529 607/59 |
| 2007/0203543 A1* | 8/2007 | Stone | A61N 1/37247 607/59 |
| 2007/0203546 A1* | 8/2007 | Stone | A61N 1/0529 607/59 |
| 2008/0171930 A1* | 7/2008 | Abolfathi | A61B 90/11 600/410 |
| 2009/0112278 A1* | 4/2009 | Wingeier | A61B 5/6864 607/45 |
| 2009/0171184 A1* | 7/2009 | Jenkins | A61B 5/7435 600/411 |
| 2010/0042111 A1* | 2/2010 | Qureshi | F16M 11/14 606/130 |
| 2013/0030408 A1* | 1/2013 | Piferi | A61B 5/055 604/500 |
| 2016/0367331 A1* | 12/2016 | Nelson | A61B 90/11 |
| 2017/0020623 A1* | 1/2017 | Glossop | A61B 90/11 |

* cited by examiner

STEREOTACTIC DEVICE FOR IMPLANTATION OF PERMANENT IMPLANTS INTO A RODENT BRAIN

BACKGROUND

Stereotactic devices are used for accurate surgical positioning of probes, electrodes, catheters, and other intra-body devices, such as in the brain, spine, lung, and liver. Stereotactic surgical procedures to place these types of devices within body or tissue can require accuracy to within millimeters or even micrometers. Such accuracy can depend upon the stereotactic devices used to guide the intra-body devices to specific points in the body.

Placement of intracranial devices requires particular accuracy. There are several types of stereotactic devices used for guiding and placing intracranial devices. Some of these devices fix the position of the head and utilize a Cartesian coordinate system to relate the known features on skull to an external grid. Others use a frame system that attaches to the skull and utilize a polar coordinate system to relate features on the skull to the known locations of other features. One specific system requires a burr-hole be drilled into the skull and the stereotactic device is affixed within the burr-hole. The stereotactic device is then used to guide intracranial devices into the brain through the burr-hole.

Stereotactic devices utilized for implantation of devices in humans can be quite different than those used for implantation into animals. Even stereotactic devices used for animal implantations can be different for different animal species. The differences in anatomy, size, orientation of features, and points of attachment necessitate different types of stereotactic devices for different species.

Another issue is intracranial devices that are permanently or semi-permanently emplaced for long term treatment, therapies, or research. Such intracranial devices often have externally exposed ends, protruding outside the body. The exposed ends should be supported to ensure that the intracranial placed devices remain in position. Those that provide a direct conduit into the body need to be covered to ensure that undesirable materials are not introduced into the brain. Intracranial devices implanted in animals can be particularly problematic, since the animal will often actively attempt to remove or displace the exposed ends.

BRIEF SUMMARY

Embodiments of the subject invention address the problems of accurately placing and supporting intracranial devices on subjects (e.g., subject of different species) by providing an external stereotactic system that can be partly customized to the skull anatomy of a specific subject (e.g., a specific species). Components of the stereotactic system allow intracranial implant devices to be pre-arranged to the appropriate direction and depth before implantation. Advantageously, components of the stereotactic system can be attached directly to the skull to support and contain the exposed ends of the intracranial devices. A stereotactic system customized for a specific species can be used on individuals within the species with higher accuracy and more comfortable and secure permanent or semi-permanent placement on the skull.

Prior to a neurosurgical procedure, it is not uncommon to obtain a 3-dimensional (3D) image of the brain, skull, and other structures, so that placement of intracranial devices can be pre-planned. Likewise, such 3-D images can also be used to customize components of the stereotactic system and pre-plan the placement of intracranial devices, using components of the stereotactic system of the subject invention. There are a variety of methods and techniques available for obtaining 3-D images and the invention is not limited to the method or technique used. The stereotactic system can include a surgical stencil with one or more surfaces customized to match an operating area of the skull anatomy of a specific species. The scanned or imaged operating area of the skull can be used to customize edges and surfaces of components of a stereotactic system of the subject invention.

The surgical stencil can be matched to the operating area of the skull through which the intracranial devices will be inserted into the brain. The surgical stencil can also have openings that match the location where an intracranial device will enter the brain. The customized surgical stencil can be placed directly against the subject's skull, using known landmarks. The bregma and/or lambda landmarks can be used, and the surgical stencil can be placed relative to the location of these landmarks. The surgical stencil can include additional holes through which the surgical stencil can be secured to the skull, such as, for example, with temporary screws. Once the customized surgical stencil is positioned and temporarily secured to the skull, the marking holes can be used to make indicator marks directly on the skull for later use in drilling one or more burr holes in the proper location into the skull.

In many embodiments, a stereotactic system can also include a neurocap and an implant jig, which can be used together to pre-plan, implant, and secure the placement of intracranial implants. The implant jig can provide a framework structure on which the neurocap can be placed. The implant jig can also be customized to have a space therein that models the length, width, and volume of the brain of a specific species. The neurocap can be placed on the implant jig in a precise position that mimics how the neurocap will be eventually fixed on the skull. A margin plate on the implant jig can also hold the neurocap above the space in the implant jig. Thus, placement of the neurocap on the implant jig can mimic the location of the neurocap as it would be when secured to the skull and the location relative to the brain when in that location.

The neurocap and implant jig, when combined, can provide a guide into which various intracranial devices can be inserted. The neurocap can provide a structure to which intracranial implants can be secured, and the implant jig, with the space mimicking the brain, can be used to determine the depth of intracranial implants. The implants can be inserted through the neurocap and into the space of the implant jig, which can mimic insertion of intracranial implants into the brain of the specific species.

One or more sleeves can be incorporated into the implant jig and/or the neurocap to assist with placement of intracranial implants through the neurocap and/or the implant jig. The location of the sleeves can be dictated by where the intracranial implants are to be placed in the brain. Thus, the location of the sleeves can also be customized for a particular procedure to be performed on the specific species. Furthermore, one or more of the sleeves in a neurocap can align with the sleeves in an implant jig.

After the intracranial implants are in place, the ends exposed outside the skull can be secured within the neurocap. The neurocap can be removed from the implant jig, which can expose the proximal ends of the intracranial implants or the ends of the implants that will be inserted into the brain. The neurocap implant can be positioned above the skull and oriented so that the proximal ends of the intracranial implants are aligned with the burr holes created using the surgical stencil. Using the holes formed at the bregma and lambda landmarks using the surgical stencil, the neurocap can be pushed directly downward on the skull, which will align it in the same position as the surgical stencil. This can also position the proximal ends of the intracranial implants in the same exact position in the subject's brain as they were in the space modeling the subject's brain. The neurocap can be secured to the skull to ensure that the intracranial implants remain in place.

In an embodiment, the stereotactic system can include a protective cover that can be placed over the neurocap. Once the neurocap has been emplaced and secured to the skull, the protective cover can be placed over the neurocap and removed as necessary to utilize the intracranial implant exposed ends.

Advantageously, the stereotactic system of embodiments of the subject invention can have interface surfaces that are a positive or negative representation of an area on the skull surface of an individual subject of a specific species. A negative interface surface is one that has one or more impressions, indentations, or hollows that are the reverse impression of an operating area. A positive interface surface is one that has one or more raised or 3D characteristics similar to or identical to those of an operating area. A positive interface surface of an operating area can interdigitate with or interfit with a negative interface surface of the same operating area. Thus, positive and negative interface surfaces can be fit together or seated against each other to provide more accuracy in the pre-placement and eventual implantation of intracranial implants. For example, a proximal end surface of the neurocap can be formed as a negative interface surface to compliment or couple with an operating area of an individual skull on which it will be affixed. Conversely, a distal end surface of the margin plate on an implant jig can be formed as a positive interface surface of the same area of the skull on which the neurocap will be affixed. Placement of the neurocap interface surface against the implant jig interface surface allows these two surfaces to be at least partially to substantially interfit or coupled together in close proximity. This increased proximity can increase the accuracy in placing the intracranial implants.

In many embodiments, a stereotactic system can be customized or adapted for use with general characteristics for a specific species. Components can also be further customized with interfacing surfaces that model the actual surface area of an individual of a specific species. Components also allow configuration and placement of intracranial implants to be determined prior to actual implantation within a subject. The interfacing of certain surfaces on components of the stereotactic system provides greater accuracy in implant placement for a specific species.

BRIEF DESCRIPTION OF THE DRAWINGS

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings.

DETAILED DESCRIPTION

Figure 1:
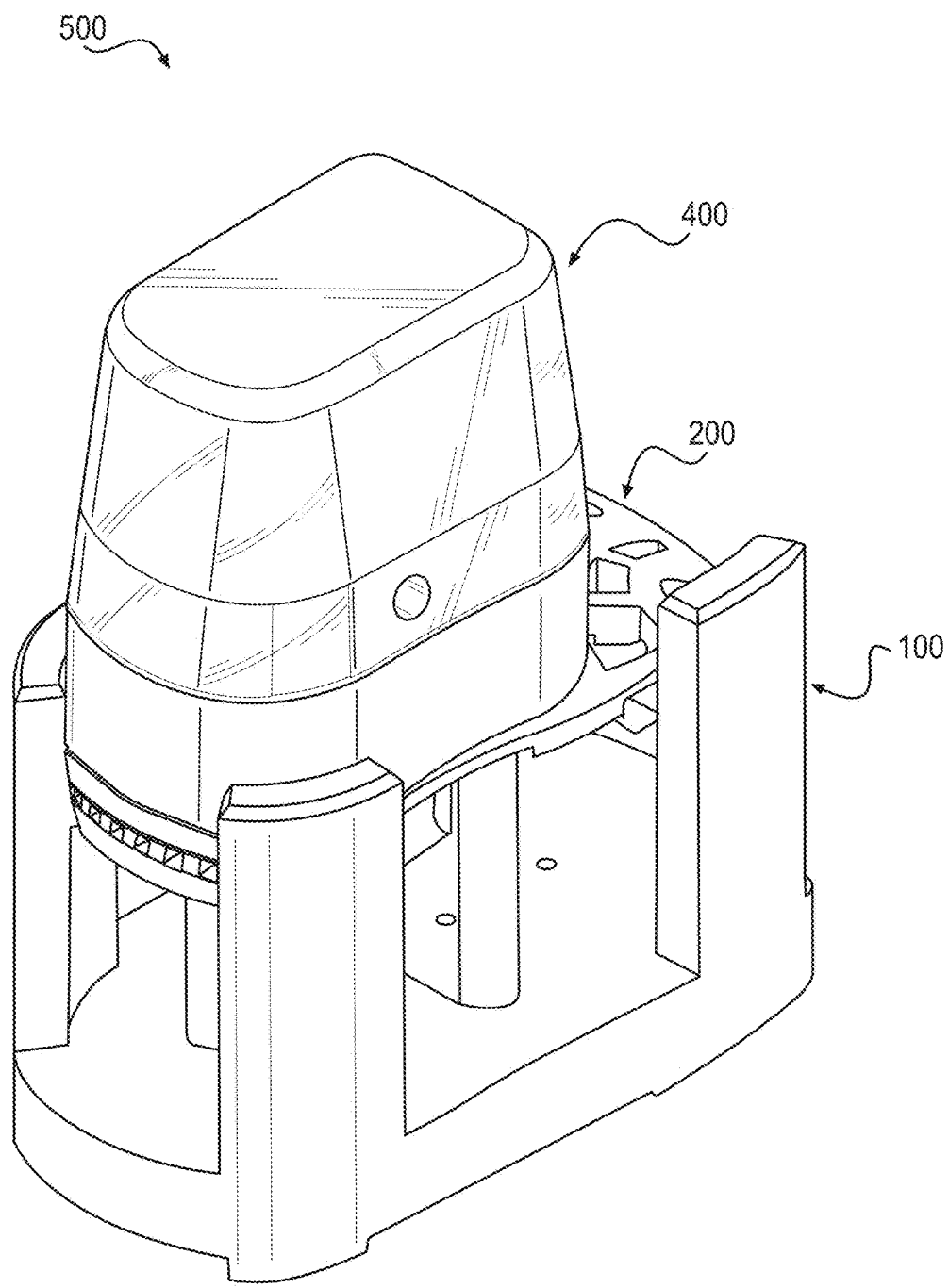
FIG. 1 is an illustration of a stereotactic system, without the stencil, according to an embodiment of the subject invention.

Embodiments of the subject invention pertain to stereotactic systems useful for implanting and securing intracranial or other types of implants. More specifically, stereotactic systems with components that can be customized for implanting and securing intracranial implants into the brain of a specific species are provided. The components of a stereotactic system can also have customized interfaces for increased accuracy in implant placement.

The following description will disclose that embodiments of the subject invention are particularly useful in the field of neurosurgical techniques, in particular the implantation of intracranial devices. However, embodiments of the subject invention are not limited to only neurosurgical applications or only to the implantation of intracranial devices. A person with skill in the art will be able to recognize numerous other uses that would be applicable to the devices and methods of the subject invention. Thus, while the subject application describes, and many of the terms herein relate to, a use for implantation of intracranial devices through the skull of a subject, other uses and modifications apparent to a person with skill in the art and having benefit of the subject disclosure are contemplated to be within the scope of the present invention.

In the description that follows, a number of terms are used in relation to the subject invention. In order to provide a clear and consistent understanding of the specification and claims, including the scope to be given such terms, the following definitions are provided.

The terms "subject" and "specific species", as used herein, describes an animal, including mammals, to which the devices and methods of the present invention can be applied and that can benefit from such application. This can include mammalian species such as, but not limited to, apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. It can also include patients that range in age from neonates to elderly.

The terms "intracranial implant" or "implant," as used herein, are merely for literary convenience. These terms can encompass any tool, mechanism, or device that can be permanently or temporarily inserted, implanted, installed, or otherwise introduced into or onto a subject in need of such treatment.

Also, as used herein, and unless otherwise specifically stated, the terms "operable communication," "operable connection," "operably connected," "cooperatively engaged" and grammatical variations thereof mean that the particular elements are connected in such a way that they cooperate to achieve their intended function or functions. The "connection" or "engagement" may be direct, or indirect, physical or remote.

It is to be understood that the figures and descriptions of embodiments of the present invention have been simplified to illustrate the elements that are relevant for a clear understanding of the invention, while eliminating, for purposes of clarity, other elements that may be well known. Those of ordinary skill in the art will recognize that other elements may be desirable and/or required in order to implement the present invention. However, because such elements are well known in the art, and because they do not facilitate a better understanding of the present invention, a detailed discussion of such elements is not provided herein.

Reference is made throughout the application to the "proximal end" or the "proximal side" and "distal end" or the "distal side." As used herein, the proximal end or proximal side is that end nearest to a subject or, for certain components described herein, the end directed towards a surface on which the component sits during use. For example, the surface of a neurocap that contacts the skull of a subject is the proximal end, as is the surface of an implant jig that sits closest to a surface during use. Conversely, the distal end or distal side is furthest from the proximal end or is that end directed away from a subject or a surface.

Reference will be made to the attached figures on which the same reference numerals are used throughout to indicate the same or similar components. With reference to the attached figures, which show certain embodiments of the subject invention, it can be seen in FIG. 1 that in an embodiment, a stereotactic system 50 can include an implant jig 100, a neurocap 200 capable of being fitted onto or seated against the implant jig. A further embodiment includes a surgical stencil 300 that can be used to create marks on the skull for later use in placement of the neurocap. There can also be a protective cap 400 that operably connects to the neurocap. Each of these general components can have one or more sub-components and features, which will be discussed in detail below.

Figure 2:
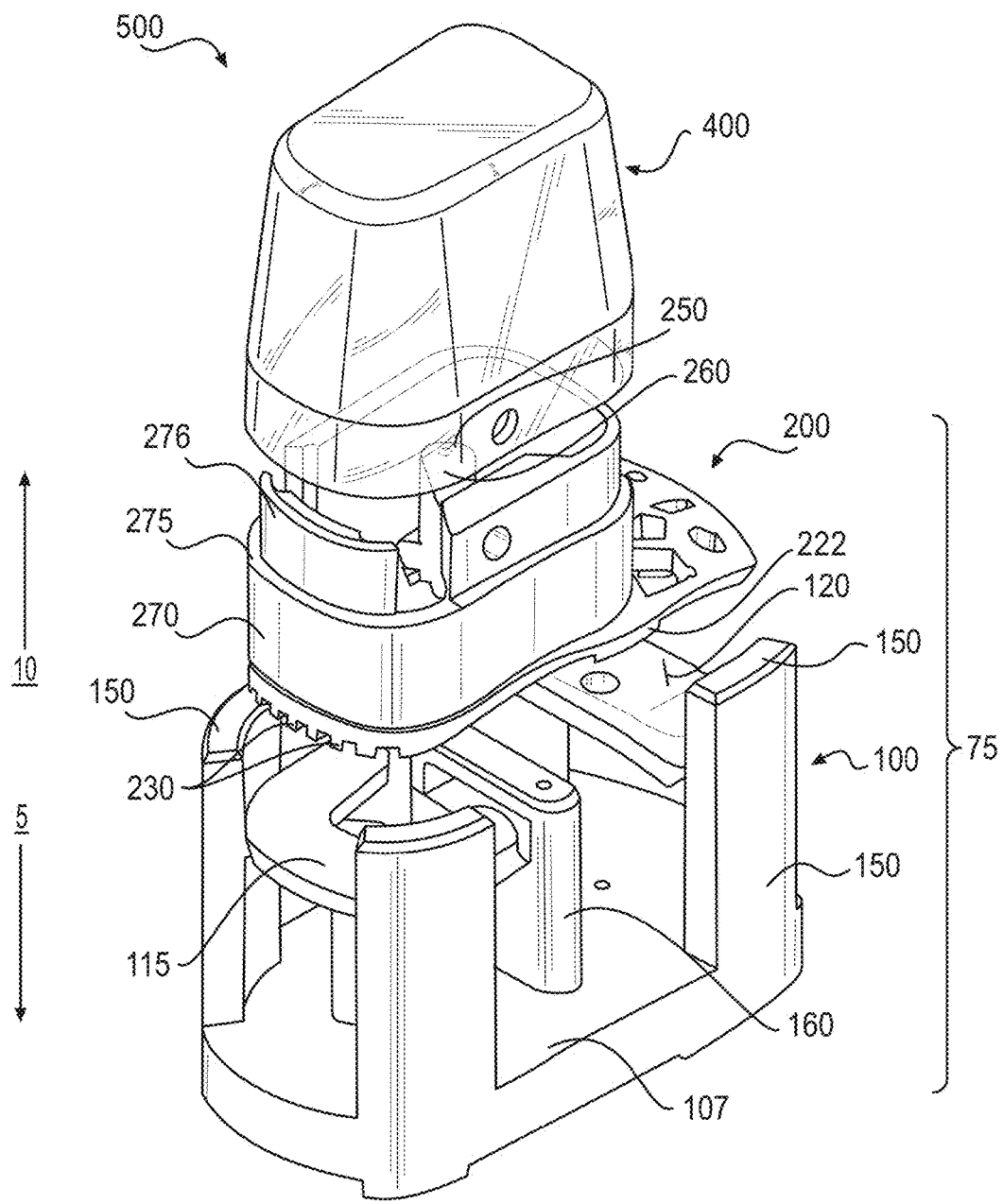
FIG. 2 is an illustration of an exploded view of a stereotactic system, without the stencil, according to an embodiment of the subject invention.

FIGS. 1 and 2 illustrate the interaction of certain components of the stereotactic system 50 and also demonstrate how surfaces of the components can interfit or be coupled. As illustrated in FIG. 2, there can be, in an embodiment, an implant jig 100 on which a neurocap 200 is configured to fit against, couple with, or seat against. When combined, these two components can be used as a guide 75 for pre-configuring, pre-planning and/or pre-placement of implants 15, prior to their implantation in a subject. Thus, a surgical implant procedure can be planned out prior to actual implementation, by utilizing the guide 75. As discussed above, the neurocap and implant jig can be at least partially tailored or customized for a specific species. For example, the volume 107 of an implant jig can model the tissue or organ of a specific species in which a target tissue area is located and the first interface surface 120 and the second interface surface 220 can each be either at least partially positively or negatively modeled after an operating area of an individual subject on which the neurocap will be attached. Thus, the guide provided by coupling of these components can be generally customized for a specific species and can be further more particularly customized for an individual subject of the specific species.

During manufacture of the components of a stereotactic system 50, information regarding the location of a target tissue area in a subject can be used to further customize the location of ports 250 within the guide, for directing implants into the organ or tissue where the target tissue area is located. For example, medical scans, images, radiographs, and other physiological data and information can be used to determine where ports should be located on a guide, to ensure that the implants are accurately directed towards the target tissue area.

Typically, intracranial implants are positioned directly into brain tissue after first reviewing and analyzing one or more images of the tissue. The image can be a 2- or 3-dimensional image on which distances and relative positions can be determined. The depth, direction, and other data regarding the placement of the implant can be determined by reviewing the image prior to the implantation procedure. The implant jig according to embodiments of the subject invention can model all or some portion of the brain volume of the specific species. Initially inserting implants, such as, for example, intracranial implants, into the implant jig, allows the depth, direction, and other factors to be pre-determined and, if necessary, corrected before the actual implantation into a subject.

Figure 4:
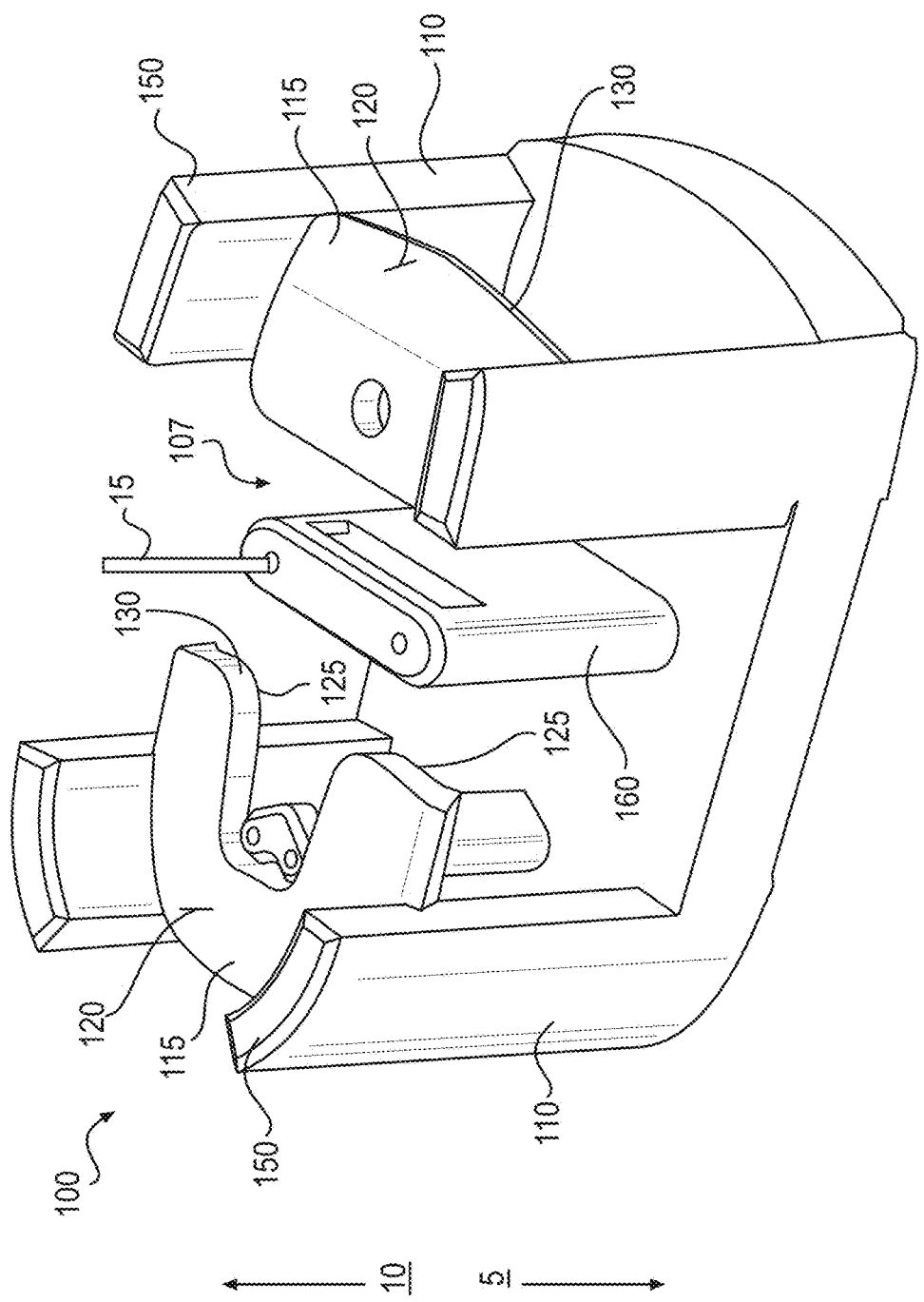
FIG. 4 is an illustration of an implant jig, according to an embodiment of the subject invention.

In an embodiment, an implant jig 100 has a support plate 105 at the proximal end 5. The support plate can provide a base to which other elements of the implant jig can be attached. FIG. 4 illustrates a non-limiting embodiment of a support plate. A support plate can have a circumferential shape similar to that of other elements of the implant jig. The support plate can also have other circumferential shapes and sizes.

Figure 3:
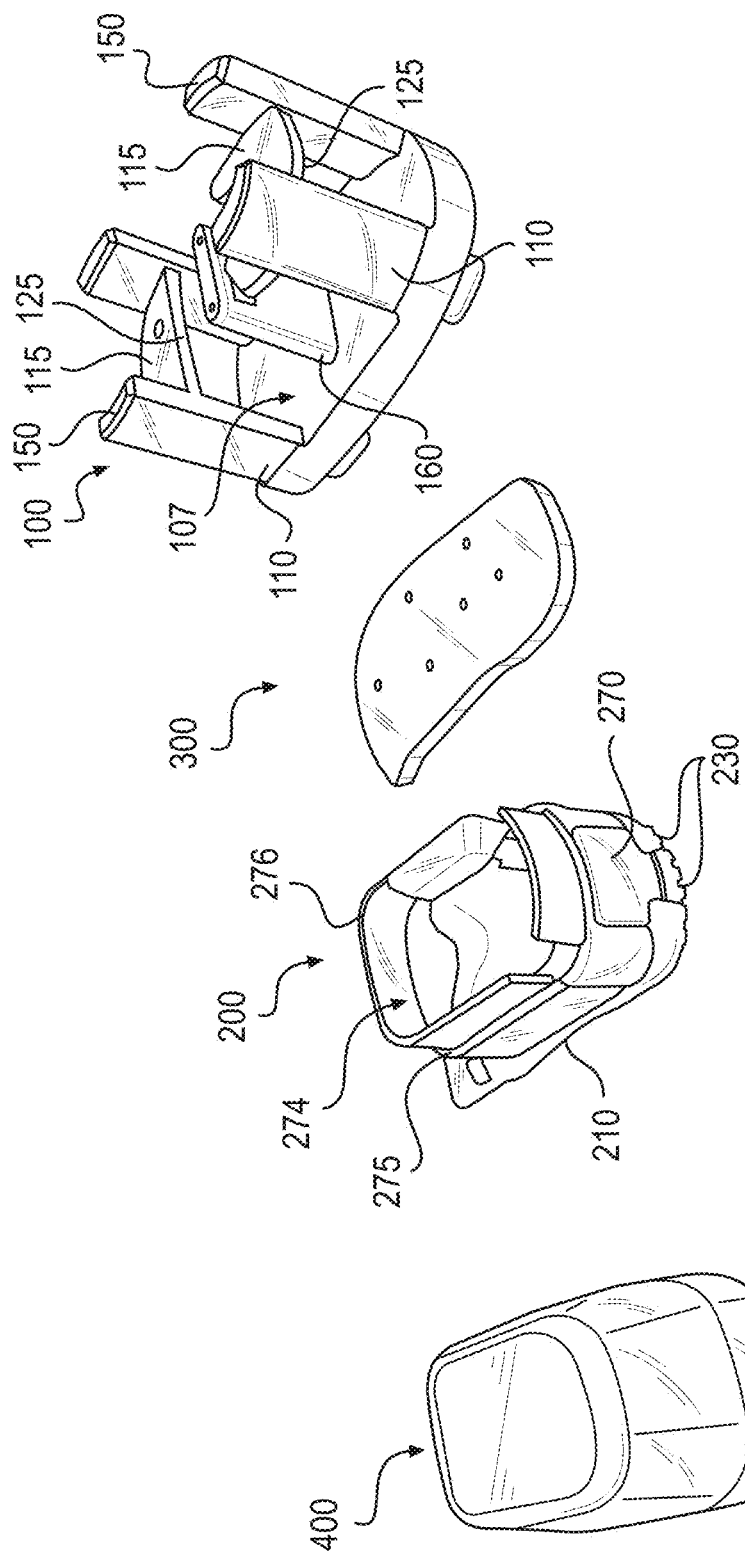
FIG. 3 is a photograph showing the disassembled components for a stereotactic system, according to an embodiment of the subject invention.
Figure 5:
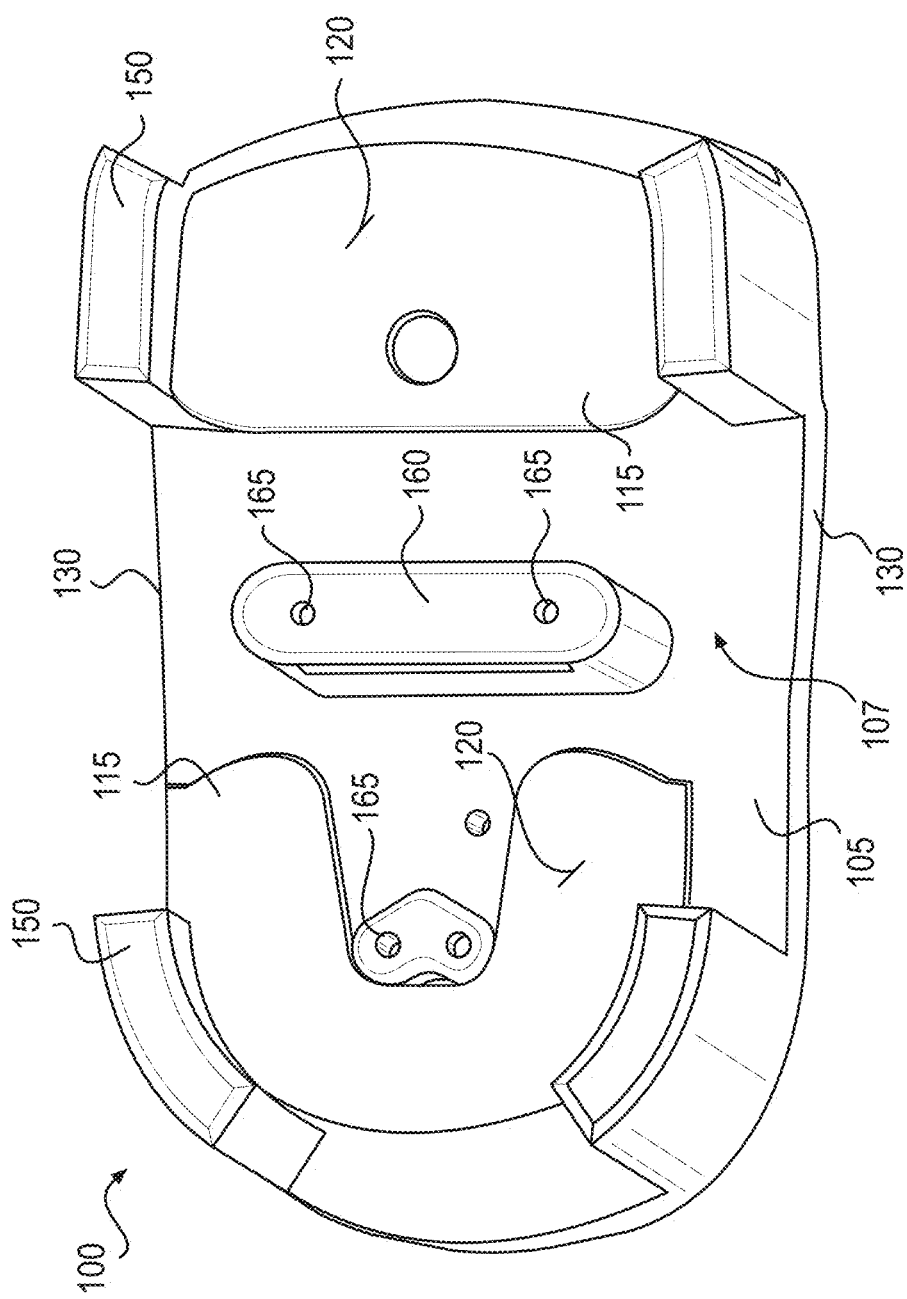
FIG. 5 is a distal plan view of the implant jig shown in FIG. 4.
Figure 13:
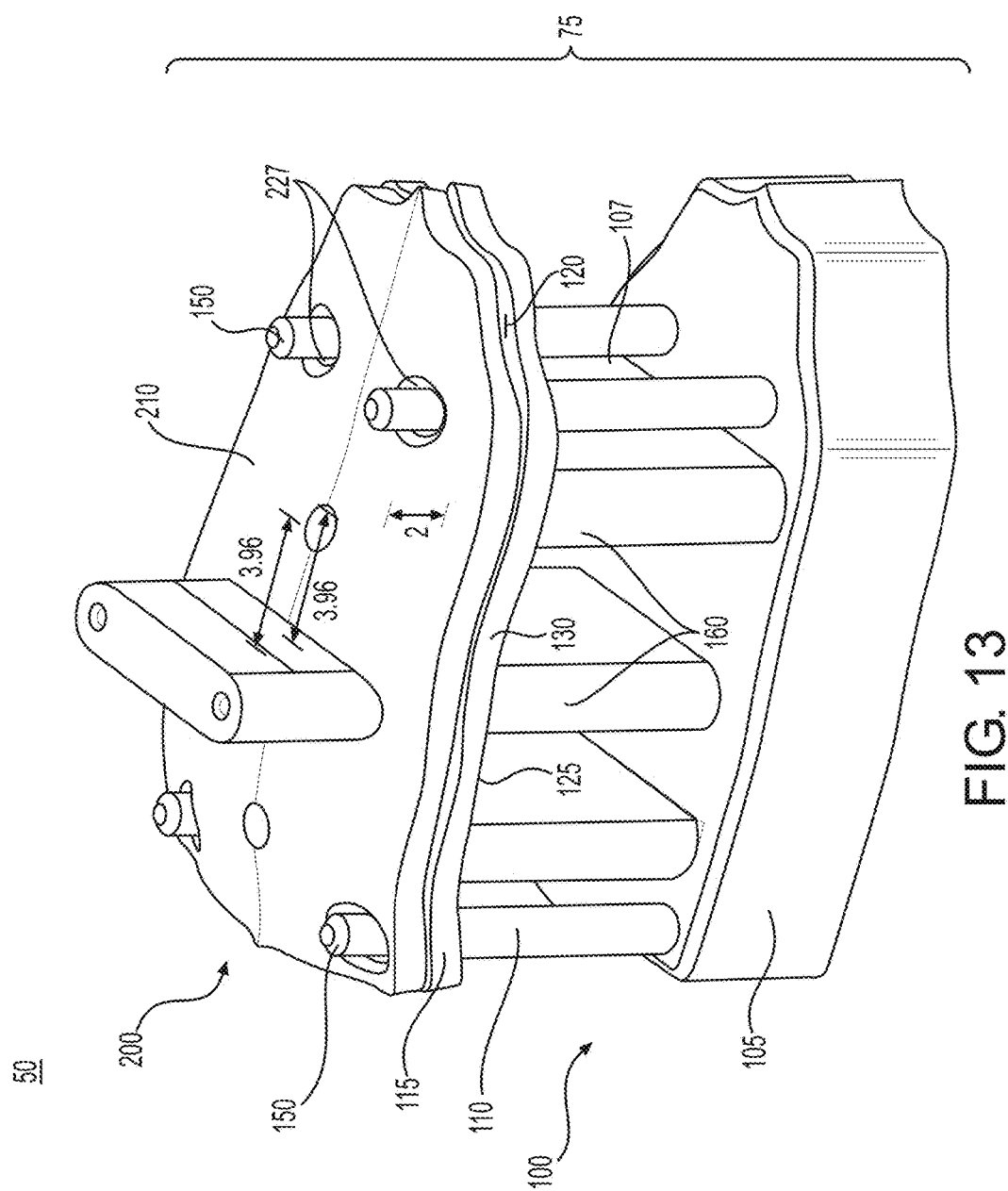
FIG. 13 is a distal side perspective view of a stereotactic system, according to an embodiment of the subject invention.
Figure 14:
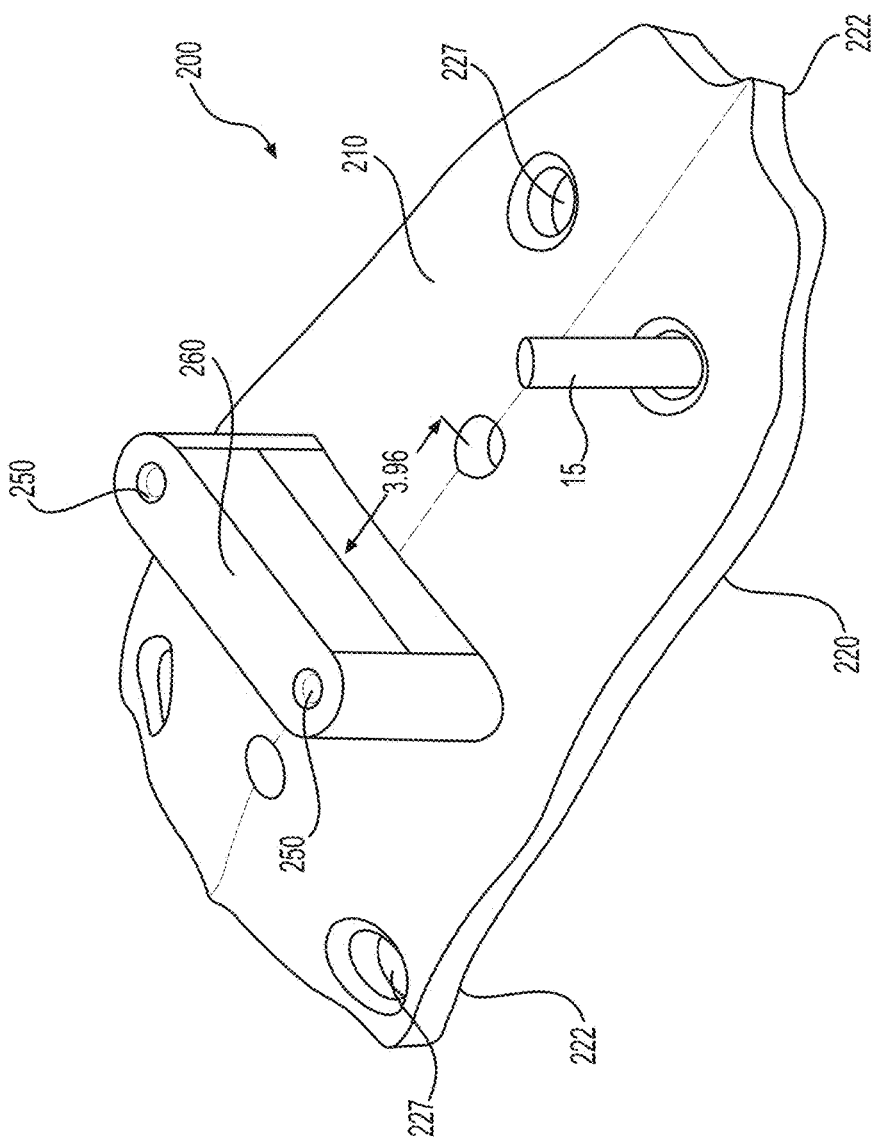
FIG. 14 is a distal side perspective view of a neurocap, according to an embodiment of the subject invention.
Figure 15:
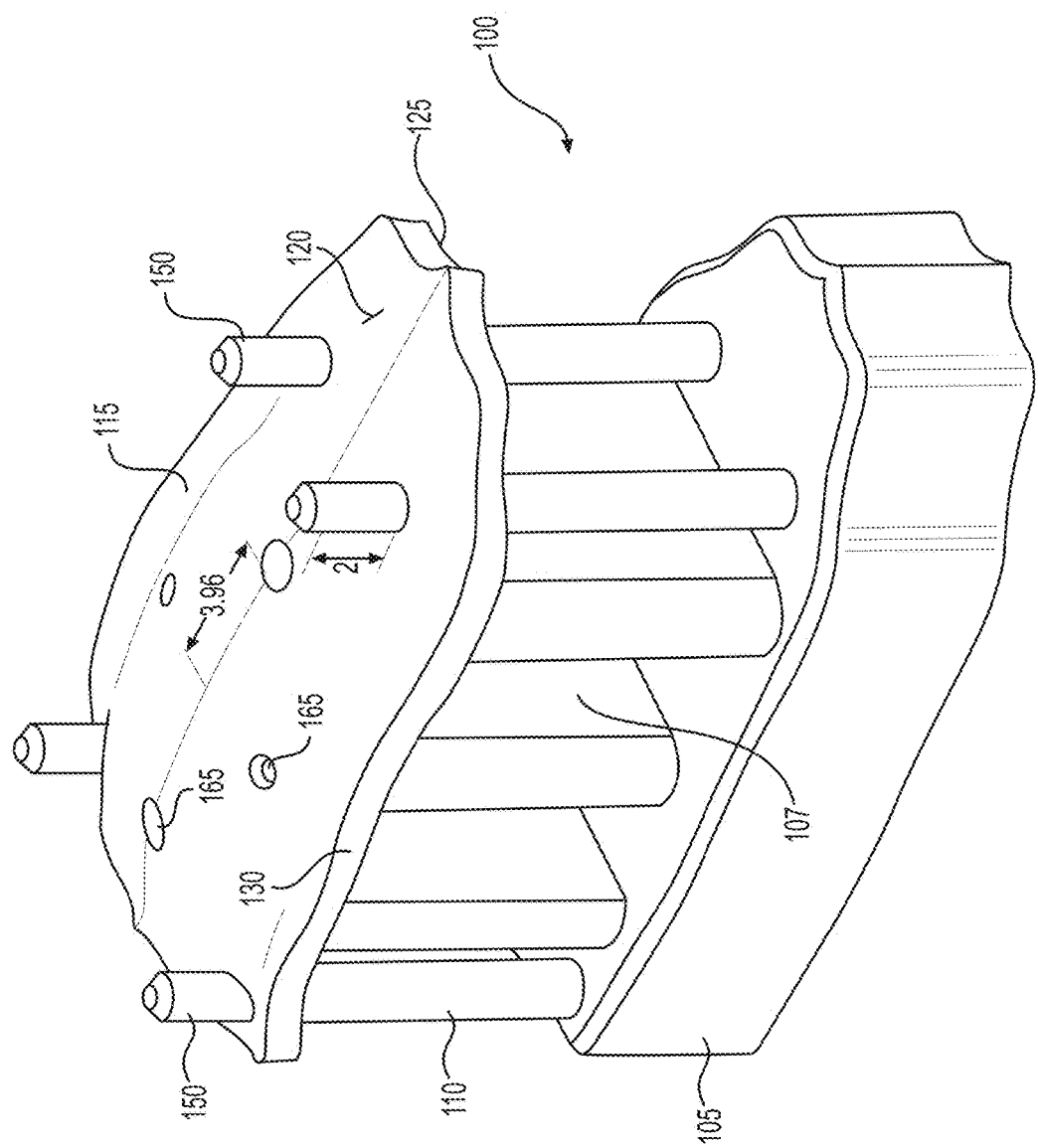
FIG. 15 is a distal side perspective view of an implant jig, according to an embodiment of the subject invention.

The implant jig can be configured to encompass a volume 107 that models the brain volume, or some part thereof, in which the implants will eventually be inserted to reach a target tissue area 25. By way of non-limiting example, the implant jig can be configured to generally model the volume of the brain of a specific species. FIGS. 4, 5, and 15 illustrate embodiments of an implant jig having a volume 107 that models the rat brain. In an embodiment, attached to the support plate 105 there can be at least two posts 110 extending upwards from the support plate and towards the distal end 10. The posts on the support plate can establish a circumferential boundary for the volume 107 being modeled. In a particular embodiment, at least four posts are attached to the support plate, where there is at least one at or near the corners of the support plate. FIGS. 13 and 15 illustrate an example of this embodiment. In a further particular embodiment, the posts can have a curvilinear shape that more accurately defines a circumferential boundary for the volume being modeled. FIGS. 3, 4, and 5 illustrate an example of this where the posts have a curvature along their length that defines or approximately defines the circumferential boundary of the volume. FIGS. 13, 14, and 15 illustrate an alternative embodiment where the posts on a support plate to not necessarily define a circumferential boundary.

Embodiments of the subject invention can be useful with implants that traverse a margin or some surface of the body in order to acquire access to a target tissue area 25. For example, catheters, probes, electrodes, needles, and other types of elongated implants can be inserted through the skull to reach a target tissue area 25 in the brain. Embodiments of the subject invention can establish an uppermost boundary of the volume 107 that corresponds to that of an operating area on the skull. As mentioned above and explained in more detail below, a neurocap can be used with the implant jig to pre-position implants in the neurocap for later implantation into a subject. Modeling the operating area of the skull on which a neurocap can be attached can improve the accuracy of implant placement in both the neurocap and later in the brain.

In an embodiment, one or more margin plates 115 can be operably connected to one or more of the posts 110, as shown, for example, in FIGS. 3, 4, 5, and 15. A margin plate can be operably connected to at least one post in a location that would form a volume 107 under the proximal side 5 of the margin plate, where the volume models, or generally models, that of the brain of a specific species. FIG. 3 shows a non-limiting example of two margin plates 115 each operably connected to two of four posts 110 attached to the support plate, where the volume 107 formed beneath the proximal side 5 of the margin plate 115 models that of the brain of a rat. In other words, a margin plate can represent the layer, surface, or other covering that an implant would pass through to reach an underlying tissue or organ. For example, a margin plate can model a portion of the skull of a specific species through which implants will be inserted.

One or more surfaces of a margin plate 115 can beneficially also model the shape, configuration, thickness, contours, and/or other surface details 23 of an operating area 20 corresponding to that of a subject of a specific species. This can make pre-positioning of the implants more accurate, as it can allow for adjustments due to individual physiological features. In an embodiment, the margin plate has a first interface surface 120 at the distal side 10. In an embodiment, the first interface surface can have a smooth or uniform appearance, such that there is minimal or no detail, but that has contours that generally model the skull surface. In an alternative embodiment, there can be at least one feature, contour, landmark, or other detail modeled after that of an outer layer, exterior, edge, margin, or other portion of an operating area 20. For example, the first interface surface 120 can have one or more features that are a positive model of those of an operating area on the skull of a specific species through which implants will be inserted. FIG. 4 illustrates an example of a first interface surface on an implant jig with features that are a generally positively model those of an actual operating area. FIG. 15 shows an example of a first interface surface with features that more accurately positively model those that would appear on an actual tissue or organ, here the surface of a skull.

One or more images of a tissue are usually acquired before placing implants. The images can be used to pre-determine the location, depth, angle, and other factors for placement of implants. An implant jig 100 can be utilized in conjunction with such images to determine the placement of implants in a tissue. In an embodiment, the implant jig has indicators that can be used to assist with determining the placement of the implants. As will be discussed below, a neurocap can be utilized with the implant jig to secure implants in the correct positions for later insertion into a tissue. The amount of detail incorporated into the first interface surface 120 can depend upon a variety of factors, such as, for example, the method or technique employed to manufacture the margin plate, the method or technique by which the surface details are acquired, the level of accuracy necessary for the implant procedure, and other factors known to those with skill in the art.

In a further embodiment, the margin plate has at the proximal side 5 an interior surface 125. The location of the interior surface, with regard to the attachment of the margin plate 115 to the posts 110, can establish the volume 107 modeled by the implant jig 100. As with the interface surface 120 on the distal side 10, the detail of the interior surface 125 can assist in more accurate placement of implants, as it can allow for adjustments based on natural physiological features. In an embodiment, the interior surface is smooth or has minimal details. FIG. 4 illustrates an example where the interior surface has smooth surfaces with some general curvature that models an area of a skull. FIG. 15 illustrates an example where the interior surface has pronounced curvature and contours that more accurately model an area of a skull.

The implant jig 100 can model the surface and underlying tissue in which implants will be inserted. As mentioned above, a neurocap 200 can be coupled or seated against the first interface surface of a margin plate 115 of an implant jig to assist with pre-placement of implants into the neurocap. Thus, a margin plate that provides a sufficiently accurate representation of the skull area over which the neurocap will be attached can be beneficial in placement of implants. In an embodiment, the edge 130 of a margin plate on an implant jig can also be a model of the circumference of the operating area 20 against which a neurocap will be attached. FIGS. 1, 2, and 13 illustrate an example of a margin plate having an edge 130 that is generally similar to the circumference of the operating area 20 and a neurocap 200 placed against the margin plate and coupled with an implant jig. FIGS. 5 and 15 illustrate examples of a margin plate 115 with edges 130 that model the circumference of the operating area 20.

Furthermore, implants can be inserted through the neurocap and into the volume 107 of the implant jig. This can require exerting pressure against a margin plate, which can distort the margin plate and affect accuracy of the implant placement. In a further embodiment, the implant jig includes stanchions 160 that rise from the support plate 105 in strategic locations to contact the proximal end 5 of a neurocap. The stanchions can support the neurocap and inhibit distortion of the margin plates during placement of implants therein. Examples of stanchions can be seen in FIGS. 3, 4, 5, and 13.

The neurocap 200 component of the stereotactic system 50 can be utilized for placing implants 15 into the target tissue area 25 through the operating area 20. The neurocap can be attached to an area of the body through which the implants will be inserted, such as, for example, the exterior of skull for accessing brain tissue. The neurocap can be pre-configured to receive implants at specific locations. These pre-configured locations can be made to correspond to the target tissue area 25 in a brain where the implant will be directed. By way of non-limiting example, a neurocap can be affixed to the skull over an operating area 20. The implants 15 pre-positioned within the neurocap can then be pushed or otherwise moved through the neurocap, through the operating area and into the brain until the implant or some part thereof reaches the target tissue area 25. The distance by which the implants 15 are pushed through a neurocap can be determined in advance by utilizing an implant jig 100, described above.

Figure 6:
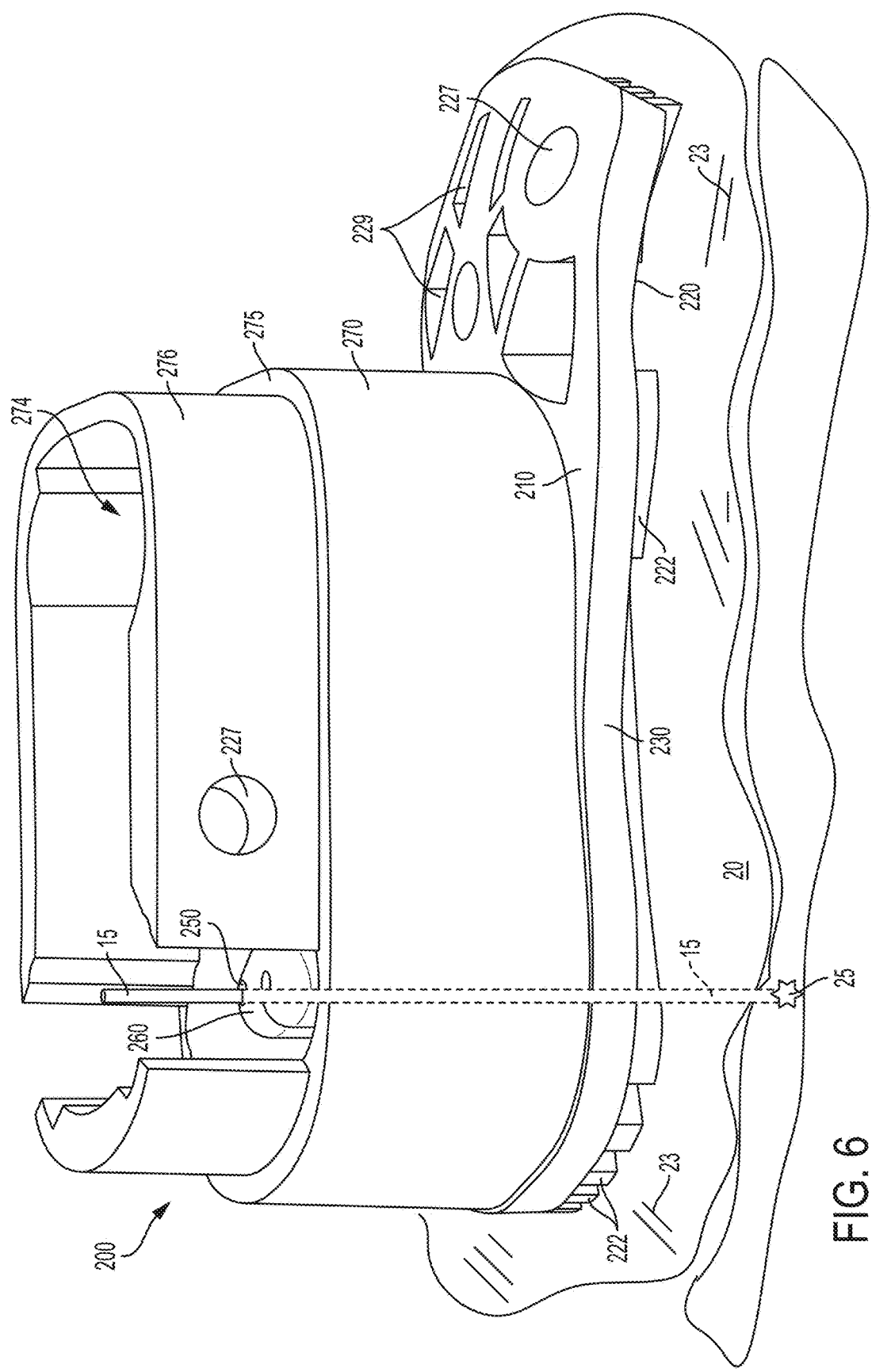
FIG. 6 is a distal end side perspective view of a neurocap, according to an embodiment of the subject invention. Also shown is the neurocap contacting an operating area.

In an embodiment, a neurocap 200 has an interface plate 210 that can be positioned against the operating area 20 and attached, permanently or removably, to secure the position of an implant 15. FIG. 6 illustrates a non-limiting example. Prior to being attached to the operating area 20, the interface plate 210 can be coupled to the one or more margin plates 115 on an implant jig 100, for pre-placement of implants in the neurocap. In an embodiment, the interface plate has at least one second interface surface 220 on the proximal side 5 that contacts the at least one first interface surface 120 on the distal side 10 of a margin plate. As mentioned above, it can be beneficial for the first interface surface to accurately couple and align with the second interface surface to ensure accuracy in placement of implants in the neurocap and later to a target tissue area 25. In an embodiment, the second interface is a negative model of the operating area, which can allow the second interface surface to be interfit with the first interface surface and interfit with the operating area when the neurocap is attached.

To assist with the placement of the interface plate 200 against one or more margin plates 100, an implant jig 100 can have alignment structures 150 thereon. In an embodiment, an implant jig can have alignment posts that extend above a margin plate, so that they are distal to the first interface surface. The alignment posts can, though are not required to, correspond to the location of the posts 110, such as shown, for example, in FIGS. 13 and 15. In a further embodiment, the interface plate 200 has one or more alignment holes 225 that fit over the support posts of an implant jig 100. FIG. 13 illustrates one example of alignment holes on alignment posts. In an alternative embodiment, one or more alignment posts can be positioned or configured so that a margin plate can be fittingly positioned between them with minimal tolerance for accurate alignment with a margin plate. FIGS. 1 and 2 illustrate an example of alignment posts configured or shaped to fit against or conform to an outside edge 230 of an interface plate 200. With this embodiment, the alignment posts can correspond to the location of the support posts, but this is not required and the alignment posts can arise from anywhere on a margin plate or the support plate.

Once the interface plate 200 is aligned with the one or more margin plates, the first interface surface 120 can contact the second interface surface 220. As mentioned above, the contact between these two surfaces can model the contact that the interface plate will make with the operating area 20. Thus, the accuracy with which the first interface surface 120 and the second interface surface 220 make contact can affect the accuracy with which implants 15 positioned on the neurocap 200 will reach the target tissue area 25. The characteristics of a first interface surface have been discussed above and are reasserted here with regard to a second interface surface. In a particular embodiment, the second interface surface has contours, structures, or other details that allow it to sit or couple securely with a margin plate, but do not, necessarily, model the surface details of an operating area. FIGS. 2, 3, and 6 illustrate an embodiment where the second interface surface has complementary details 222 that can interdigitate or interfit with physiological details 23 of the operating area 20. In another particular embodiment, the second interface surface has contours that more closely model the surface details 23 of an operating area, so that the first and second interface surfaces can coincide more fully and/or be accurately coupled. FIGS. 13 and 14 illustrate an example of this, where the first and second interface surfaces have contours and features that more closely fit together or coincide with each other. The contours of the second interface surface can also model natural details of an operating area, so that when the neurocap is placed against an operating area the second interface surface will coincide with the natural details 23 of the operating area.

The attachment of a neurocap 200 to an operating area can be accomplished by a variety of techniques known in the art. For example, screws, plugs, pins, various adhesives, other devices or materials, and/or combinations thereof can be used. In an embodiment, the neurocap is both screwed onto the target area of the skull and an adhesive is used. In a further embodiment, a neurocap has one or more bores 227 for receiving a screw or other connector. In still a further embodiment, the interface plate 210 has one or more cutouts 229 therein that allow an adhesive to pass through to secure the interface plate to an operating area.

In a further embodiment, a neurocap has at least one port 250 through which an implant can be inserted. The at least one port can pass through the interface plate and lead into the volume 107 of an implant jig 100, such that the appropriate depth can be determined for the implant to reach the target tissue area 20. Utilizing the volume 107 as a model, an implant can be inserted to the correct depth and angle to reach the target tissue area 25. For example, if the volume is a model for the brain of a rat, the implant can be inserted into the volume to a point that coincides with that in a living rat. The depth, angle, and other information about the implant can then be marked, measured, or otherwise recorded and then the implant removed from the volume and/or the neurocap. The port can also have a friction fit with the implant or be otherwise securable within the port, allowing the implant to remain in the port after being removed from the implant jig volume. When the neurocap is affixed to the operating area, the implants can then be pushed or moved to the pre-measured or pre-recorded depth, which should place the proximal end of the implant in or sufficiently near the target tissue area.

Implants 15 that pass through the neurocap and to the target tissue area 25 can have exposed ends 17 that protrude from the operating area. Advantageously, the neurocap can be used to protect the exposed ends from undesirable contact and can also secure the position of the exposed ends, so that the implant is not moved from the target tissue area in the body. In an embodiment, the exposed ends are secured to the interface plate 210. In a further embodiment, the exposed ends are secured within the ports 250 in the interface plate. Any of various methods and devices can be used to secure the exposed ends in the ports, including, but not limited to, connectors, adhesives, adhesive tapes, or other apparatuses known in the art. FIG. 15 illustrates an example of an implant 15 secured to a port 250 in an interface plate 210.

Figure 7:
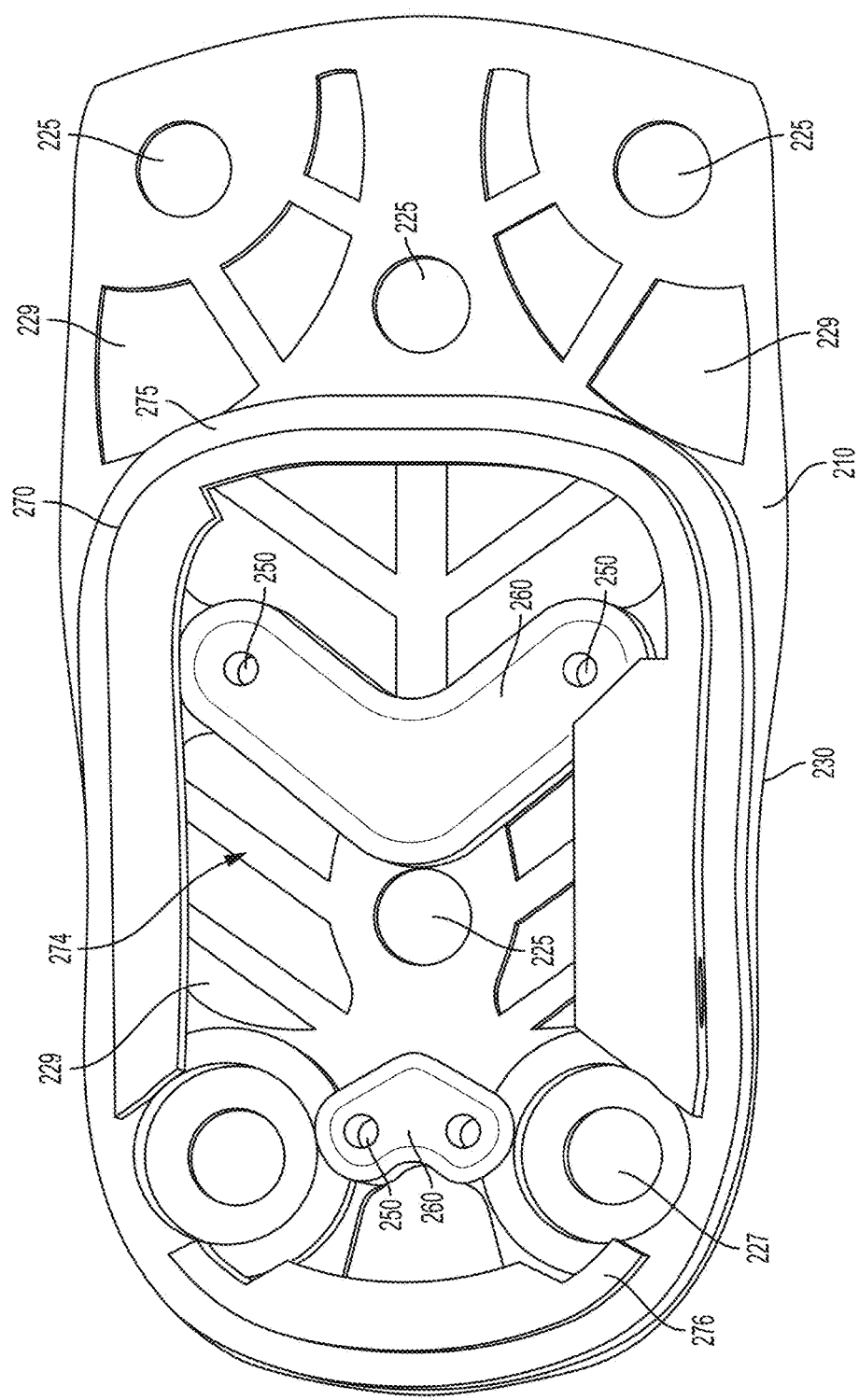
FIG. 7 is a distal end plan view of the neurocap shown in FIG. 6.

A port 25 can provide an opening in an interface plate for access to the operating area. Implants can be passed through the ports to reach the target tissue area through the operating area. In an embodiment, the at least one port is surrounded, entirely or partially, by a sleeve 260 though which an implant can pass. A sleeve can assist with aiming the implant through a port and into the body, so that it maintains the correct angle to reach a target tissue area 25. Thus, a sleeve can be directed at any angle that allows an implant to pass through a port and reach a target tissue area. FIGS. 2, 6, and 7 illustrate non-limiting examples of sleeves surrounding a port.

Customization of a guide 75 can require locating a sleeve 260 in a neurocap coinciding with the location of a stanchion 160 in an implant jig. This can be advantageous as the stanchion can be used similarly to a sleeve to guide an implant. In an embodiment, there is at least one stanchion between a support plate 105 of an implant jig and the interface plate 210 on a neurocap. In a further embodiment, the stanchion has at least one blind port 165 for receiving the proximal end 5 of an implant. In a still further embodiment, the depth of a blind port corresponds to the depth to which an implant can be inserted into the volume to reach a corresponding target tissue area 25.

In an embodiment, a neurocap 200 has a wall 270 that surrounds the one or more ports. The wall can rise from the interface plate to a sufficient height to form an interior 274 in which ports and/or sleeves, and the exposed ends of the implants, can be located. In a further embodiment, a protective cap 400 can be removably attached to or over the wall to cover the interior and further protect the ports and/or sleeves and exposed ends. To ensure that the cap remains in place, a connector can be used to removably connect the protective cap to the wall. The use of fitted caps and other types of caps are well-known. By way of example, FIGS. 1, 3, 6, and 7 illustrate a wall having a shoulder indent 275 with a lip 276 over which a protective cap can be fitted. By way of further example, the cap can be formed with an opening wide enough to fit over the wall. In a further embodiment, the indentation and the cap have matching bores 227 through which a connector can be used to removably connect the protective cap to the indentation. This can inhibit the protective cap from being accidentally knocked off or removed. A person with skill in the art will be able to determine alternative embodiments for caps or covers, including those which can resist being removed unintentionally.

Typically, when determining where to place implants, one or more landmarks on the operating area 20 or around the operating area are used for orientation. For example, the bregma and lambda suture lines present on the skulls of most animals, including humans, can be used to orient the underlying brain tissue and locations therein. A neurocap can also be positioned within or on an operating area utilizing landmarks. The neurocap can be placed on the operating area and oriented to the appropriate landmarks and marks can be made to later indicate where to place the neurocap after implants are positioned therein. In an embodiment, alignment holes 225 in a neurocap are used to visually align the neurocap to natural landmarks. For example, a neurocap can have one or more alignment holes that can be visually aligned with the bregman and lambda sutures on a skull.

Figure 8:
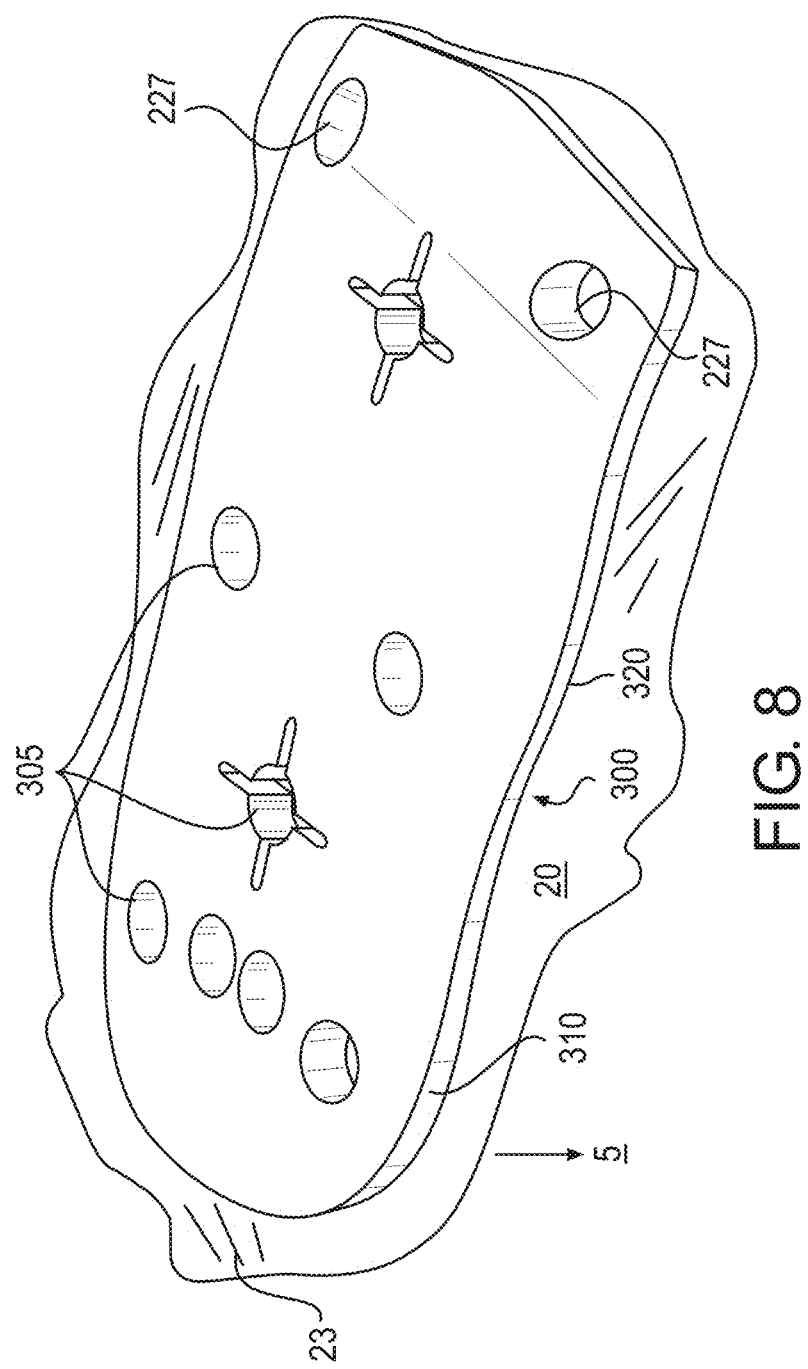
FIG. 8 is a distal end perspective view of a stencil, according to an embodiment of the subject invention. Also shown is the stencil contacting an operating area.
Figure 9:
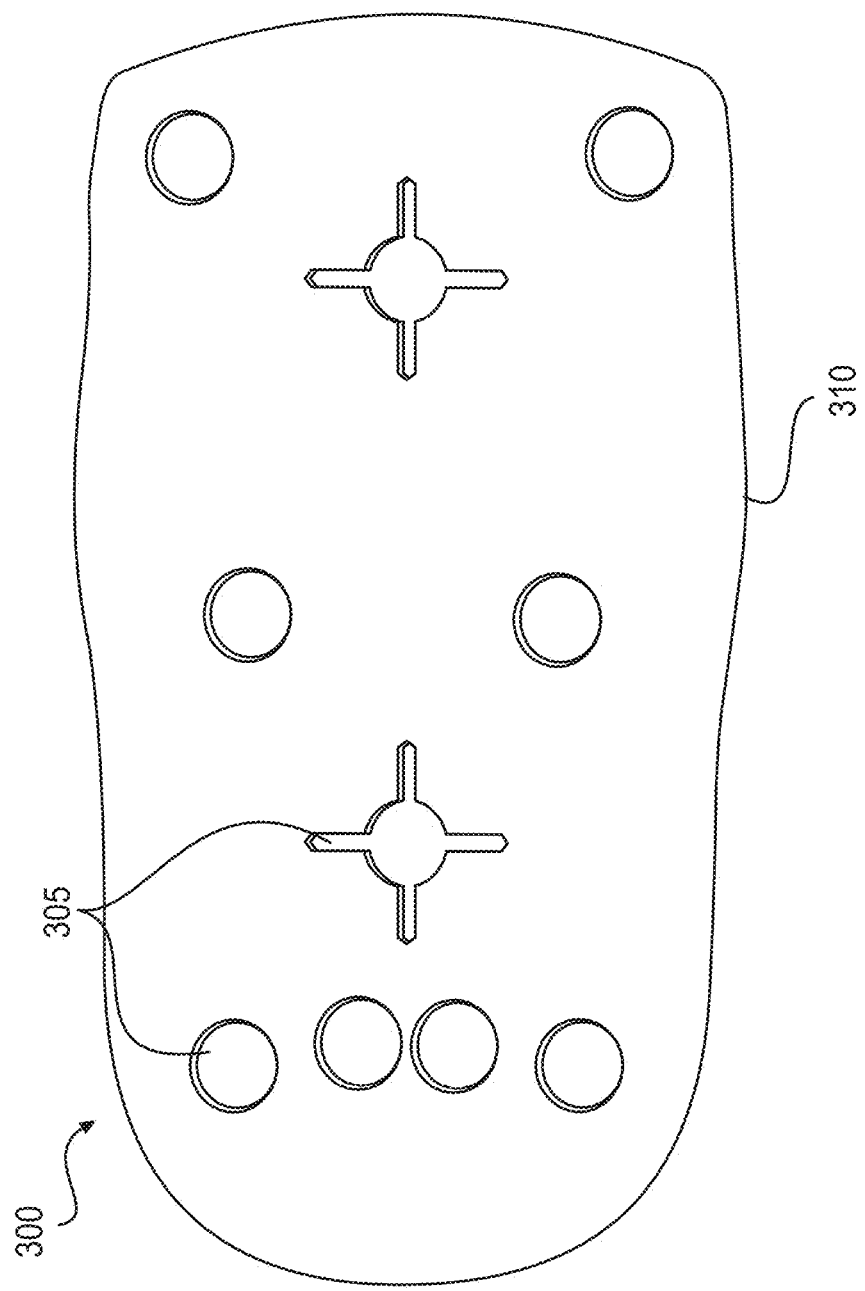
FIG. 9 is a distal end plan view of the stencil shown in FIG. 8.
Figure 10:
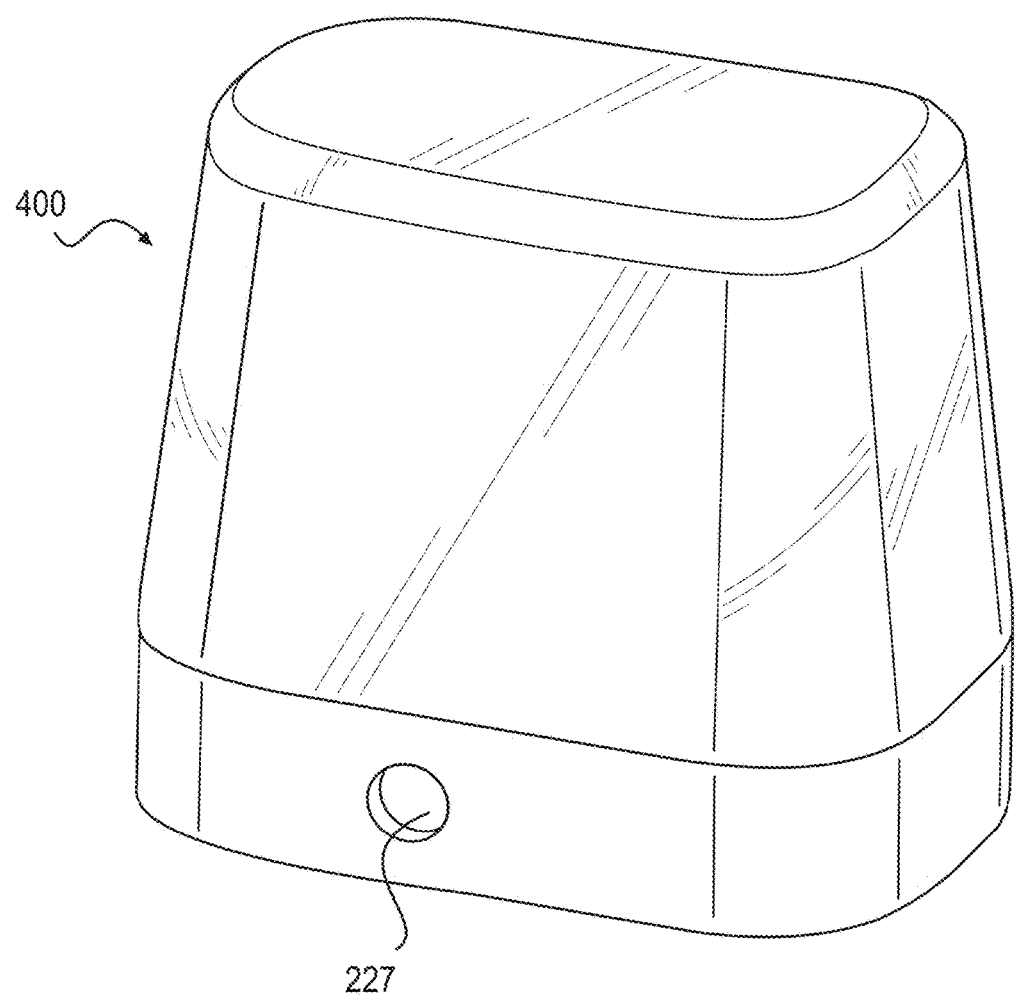
FIG. 10 is a side perspective view of a protective cap, according to an embodiment of the subject invention.
Figure 11:
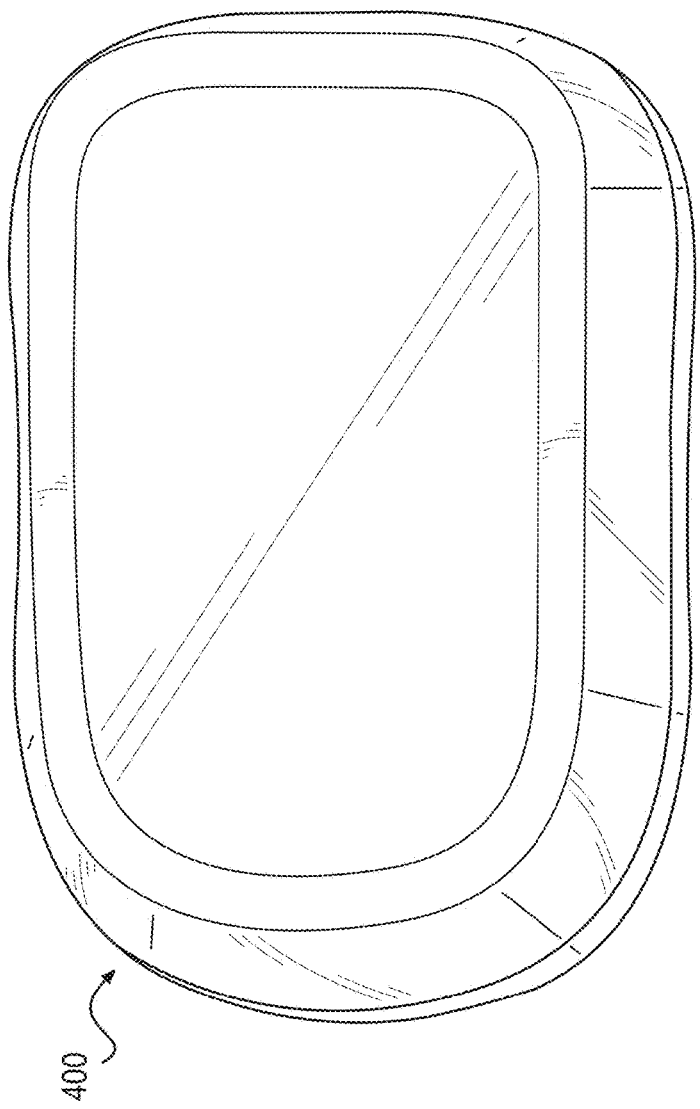
FIG. 11 is a distal end plan view of the protective cap shown in FIG. 10.
Figure 12:
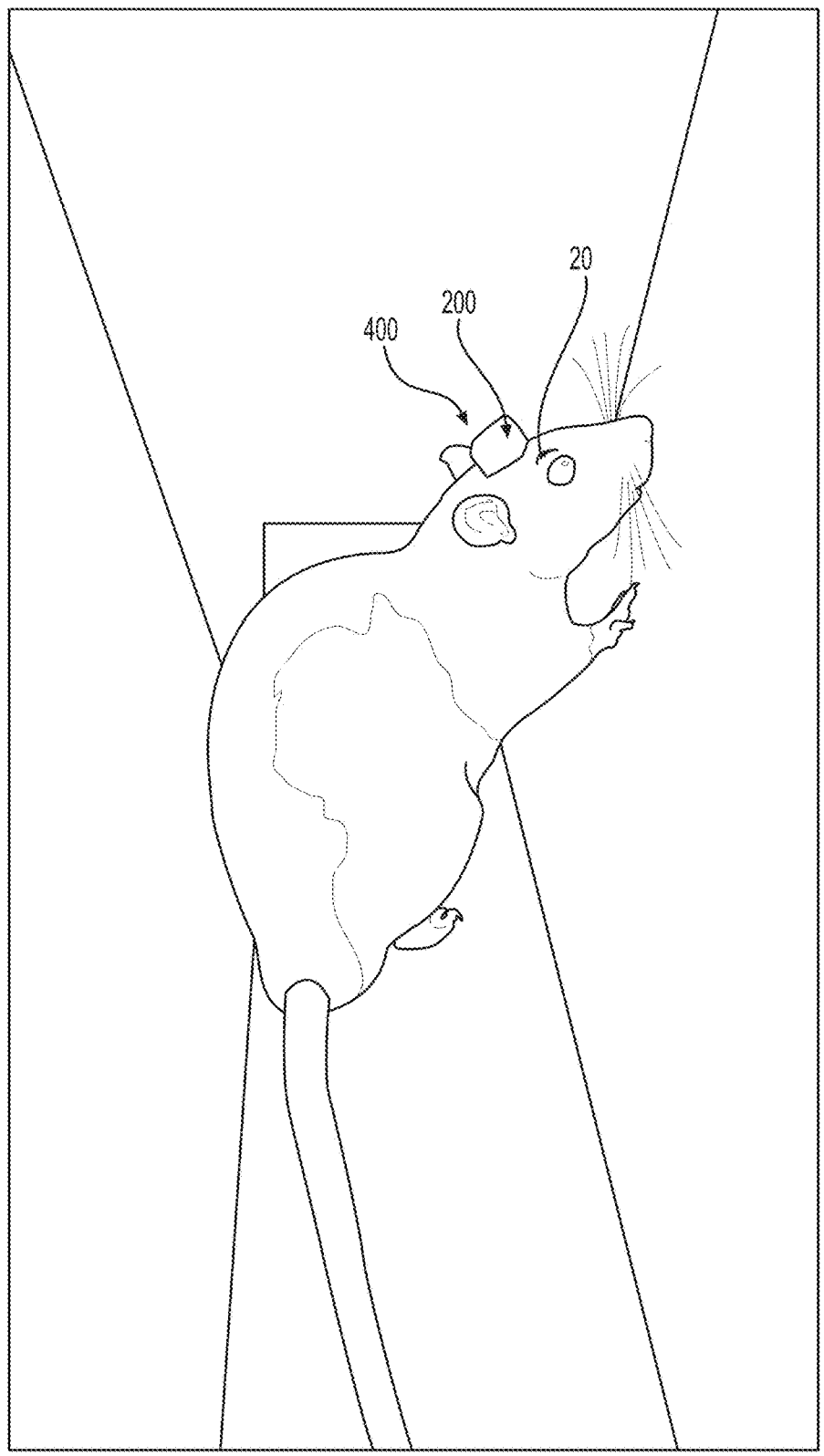
FIG. 12 is a photograph of an individual of a specific species on which a Neurocap according to an embodiment of the subject invention, with a protective cap thereon, has been attached to the skull.

A stencil 300 could also be used to determine where a neurocap 200 can be placed on the operating area 20. A stencil can have various sizes and types of openings 305 through which marks can be made on the surface of an operating area. The marks can indicate where holes need to be made in the operating area for different purposes. For example, marks can be made to indicate where holes for the attachment of connectors, for example, screws, need to be made to secure the neurocap in the operating area. Marks can also indicate where holes can be made for the passage of implants through the surface of the operating area, after a neurocap is attached. In an embodiment, the openings 305 allow for different mark shapes to be made, for later identification after the stencil is removed. For example, FIG. 9 illustrates a stencil with cross-hair openings that can be aligned with the bregma and lambda landmarks on a skull. Marks made with these openings can indicate where openings for connectors can be made later. In an embodiment, certain of the openings 305 correspond to the positions of other structures on components of a stereotactic system. By way of non-limiting example, the alignment holes 225 on a neurocap that can be used to fit onto alignment posts 150 on an implant jig 100 can also correspond to locations where connectors can be used to secure the neurocap to an operating surface. A stencil can include alignment openings that correspond to the alignment holes. FIGS. 3, 8, and 9 illustrate examples of stencils that can be used with embodiments of the subject invention.

Because the alignment and position of a stencil on an operating area 20 can later determine where a neurocap will be connected and how implants will be placed in a target tissue area, accuracy of a stencil is important. Thus, it can be advisable for the stencil to sit on or contact the operating area similarly to the way the neurocap will make contact with the operating area. As discussed above, the neurocap can have a second interface surface 220 that contacts and is attached to the operating area. In an embodiment, the stencil has a third interface surface 320 on the proximal side 5 that is sufficiently similar or identical to the second interface surface 220 on a neurocap. This similarity in interfaces can allow the neurocap to contact the operating area the same way that the stencil does, which can improve the overall accuracy of the neurocap and the implants used therewith. FIGS. 6 and 8 illustrate a non-limiting example of second interface surface 220 having protrusions 222 that, while not identical, correspond to the contours of a third interface surface 320 of a stencil.

A stencil 300 and a neurocap 200 can also have other areas that are in conformity with each other. In an embodiment, the stencil has a peripheral shaped edge 310 that corresponds to the outside edge 230 of an interface plate 210, which is illustrated by way of example in FIGS. 7 and 9. In a further embodiment, the shaped edge 310 of a stencil also corresponds to the edge 130 of an implant jig. A non-limiting example of this can be seen by comparing FIGS. 5 and 9, which show an implant jig having an edge 130 similar to the shaped edge 310 of the stencil. Thus, there can be consistency in the edge shapes, as well as the interface surfaces of components of a stereotactic system, which can all correspond to the operating area 20.

A stereotactic system according to embodiments of the subject invention can be generally configured to model an organ, tissue, or structure of a specific species. Thus, certain components of a stereotactic system 50 can be consistent in shape, configuration, placement, thickness, etc. of physiological details of a specific species. For example, the location of a wall 270 of a neurocap can be standard or consistent between stereotactic systems. Likewise, the placement of support posts 110 and stanchions 160 and margin plates 115 of an implant jig can be consistent between stereotactic systems. However, other components can be customized to model the physiological characteristics of an individual within a specific species. For example, while the position of a margin plate can be consistent, the various interface surfaces of a stereotactic system can be customized to model or closely model an operating area of an individual subject for study or treatment.

The ability to customize components of a stereotactic system 50 can depend upon the method of manufacturing the components. It can be advantageous if the manufacturing process can integrate details pertaining to the operating area, such as scans, images, photographs, tactile molds, pin molds, or haptic feedback data, radiographs, and other image or shape details obtained from various devices. In an embodiment, a scanned image of the surface of an operating area, such as on a skull, can be utilized with a 3-dimensional (3D) printing apparatus. Other techniques can also be used to import or incorporate customization data for use in 3D printing methods. For example, pin plates can be used to mold the surface of an operating area and the information from each pin can be input into the 3D printing apparatus. The 3D printing apparatus can have a template for printing certain standard, non-customized parts or areas of the system, like walls, caps, lip, support posts, but can incorporate and utilize data regarding the operating area to customize other components, like interface surfaces, ports for implants, positioning of margin plates.

Embodiments of the subject invention provide a stereotactic system that can be customized to a specific species or even to individuals within a specific species. The stereotactic system design allows for customization of only those specific components necessary to achieve the desired accuracy. This can provide accuracy in implant placement. Because certain components can model specific operating areas and the underlying tissue and organs in which a target tissue is located, it can also allow for pre-planning of implant placement. Once implant placement is determined, components can be moved from the system to the individual for placement and accurate insertion of the implants in the pre-planned locations.

Any reference in this specification to "an embodiment," "an embodiment," "example embodiment," "further embodiment," "alternative embodiment," etc., is for literary convenience. The implication is that any particular feature, structure, or characteristic described in connection with such an embodiment is included in at least an embodiment of the invention. The appearance of such phrases in various places in the specification does not necessarily refer to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section, if present) are incorporated by reference in their entirety, including all figures and tables, to the extent they are not inconsistent with the explicit teachings of this specification.

What is claimed is:

1. A method for inserting an implant into the brain of a specific species, the method comprising:
   obtaining at least one image of an operating area on a skull of a subject of the specific species;
   obtaining at least one image of a tissue corresponding to the operating area for receiving at least one implant;
   customizing a stereotactic system, which is adapted for placing implants in the specific species, the system comprising:
      an implant jig comprising:
      a support plate;
      at least one post extending from the support plate; and
      one or more margin plates affixed to the at least one post, each margin plate comprising a proximal side, a distal side, and a first interface surface on a distal side, the first interface surface at least partially modeling at least one first physiological characteristic of the operating area of the specific species and the margin plate being affixed to the at least one post in a location that models at least one second physiological characteristic of the specific species different from the first physiological characteristic;
      a neurocap, adapted to be affixed to the operating area of the specific species and comprising:
         an interface plate with a proximal side having a second interface surface that at least partially models the same at least one physiological characteristic of an operating area as that modeled by the first interface surface of the one or more margin plates, such that the second interface surface couples with the first interface surface;
         at least one port that corresponds with a location in the operating area at which an implant is to be inserted into the specific species; and
         at least one bore that corresponds with a location in the operating area at which a connector attaches the neurocap to the operating area; and
      a stencil, adapted to be temporarily placed against the operating area of the specific species, comprising a proximal side with a third interface surface that at least partially models the same at least one first physiological characteristic as the second interface surface,
   the customizing of the stereotactic system comprising utilizing the at least one image of the operating area to customize the placement of the at least one port and to customize at least one of the first interface surface, the second interface surface, and the third interface surface to have at least one third physiological characteristic corresponding to the at least one first physiological characteristic of the operating area, and utilizing the at least one image of the tissue to further customize the at least one port and to customize a volume of the implant jig to be the same or similar to that of at least one fourth physiological characteristic of the tissue to receive the at least one implant;
   utilizing the stencil of the stereotactic system to align with one or more landmarks on the skull and mark points for attachment of the neurocap and other points for the insertion of the at least one implant through the operating area;

utilizing the neurocap and implant jig to pre-determine the placement of the at least one implant through the at least one port in the neurocap into the volume of the implant jig;

recording a position of the at least one implant and retracting the at least one implant into the neurocap;

creating one or more burr holes in the operating area at the points marked using the stencil;

removing the neurocap from the implant jig and affixing the neurocap to the operating area using at least one of the burr holes; and inserting the at least one implant into the tissue through the at least one port and the at least one burr hole utilizing the recorded position.

2. The method according to claim 1, further comprising permanently affixing an exposed end of the at least one implant in the at least one port such that the position of the at least one implant in the tissue is secured.

3. The method according to claim 2, further comprising utilizing an adhesive to further attach the neurocap and to affix the exposed end of the at least one implant in the neurocap.

4. The method according to claim 2, wherein customizing the first interface surface comprises making a positive mold of an operating surface on the first interface surface, and wherein customizing the second interface surface and the third interface surface comprises making a negative mold of the operating surface on the second interface surface and the third interface surface.

5. The method according to claim 2, further comprising affixing a protective cap to the neurocap to cover the exposed end of the at least one implant.

\* \* \* \* \*